United States Patent [19]
Aramant et al.

[11] Patent Number: 6,159,218
[45] Date of Patent: Dec. 12, 2000

[54] RETINAL TISSUE IMPLANTATION TOOL

[76] Inventors: Robert B. Aramant, 5700 Fible La., Crestwood, Ky. 40014; Magdalene J. Seiler, 4312 Briarwood Rd., Louisville, Ky. 40207

[21] Appl. No.: 09/314,445

[22] Filed: May 19, 1999

[51] Int. Cl.⁷ .................................................. A61F 9/00
[52] U.S. Cl. ......................... 606/107; 128/898; 128/897; 623/6.12; 604/294; 604/59
[58] Field of Search ..................... 623/6.63, 4.1, 623/6.12; 128/898, 897; 606/107, 161, 167; 604/294, 239, 59

[56] References Cited

U.S. PATENT DOCUMENTS

| | | | |
|---|---|---|---|
| 4,715,373 | 12/1987 | Mazzocco et al. | 623/6.12 |
| 5,108,421 | 4/1992 | Fowler | 606/213 |
| 5,807,400 | 9/1998 | Chambers et al. | 606/107 |
| 5,817,075 | 10/1998 | Giungo | 604/294 |
| 5,941,250 | 8/1999 | Aramant et al. | 128/898 |

FOREIGN PATENT DOCUMENTS

| | | | |
|---|---|---|---|
| WO91/02499 | 3/1991 | WIPO | A61F 2/14 |
| WO94/21205 | 9/1994 | WIPO | A61F 9/00 |
| WO94/25569 | 11/1994 | WIPO | C12N 5/00 |
| WO96/26759 | 9/1996 | WIPO | A61M 31/00 |

*Primary Examiner*—Dinh X. Nguyen

[57] ABSTRACT

The disclosure relates to a method and instrument for implanting retinal tissue into the subretinal space of the eye comprising the steps of inducting a fragment of retinal tissue into a tubular nozzle of an instrument by retracting a mandrel telescoped internally of the nozzle, incising the pars plana region of the eye, incising the retina of the eye to expose a subretinal target area, inserting the nozzle of the instrument through the incisions in the pars plana and retina of the eye, orientating an open end of the nozzle over the target area of the retina, and retracting the nozzle relative to the mandrel of the instrument to deposit the tissue in the target area of the eye.

6 Claims, 3 Drawing Sheets

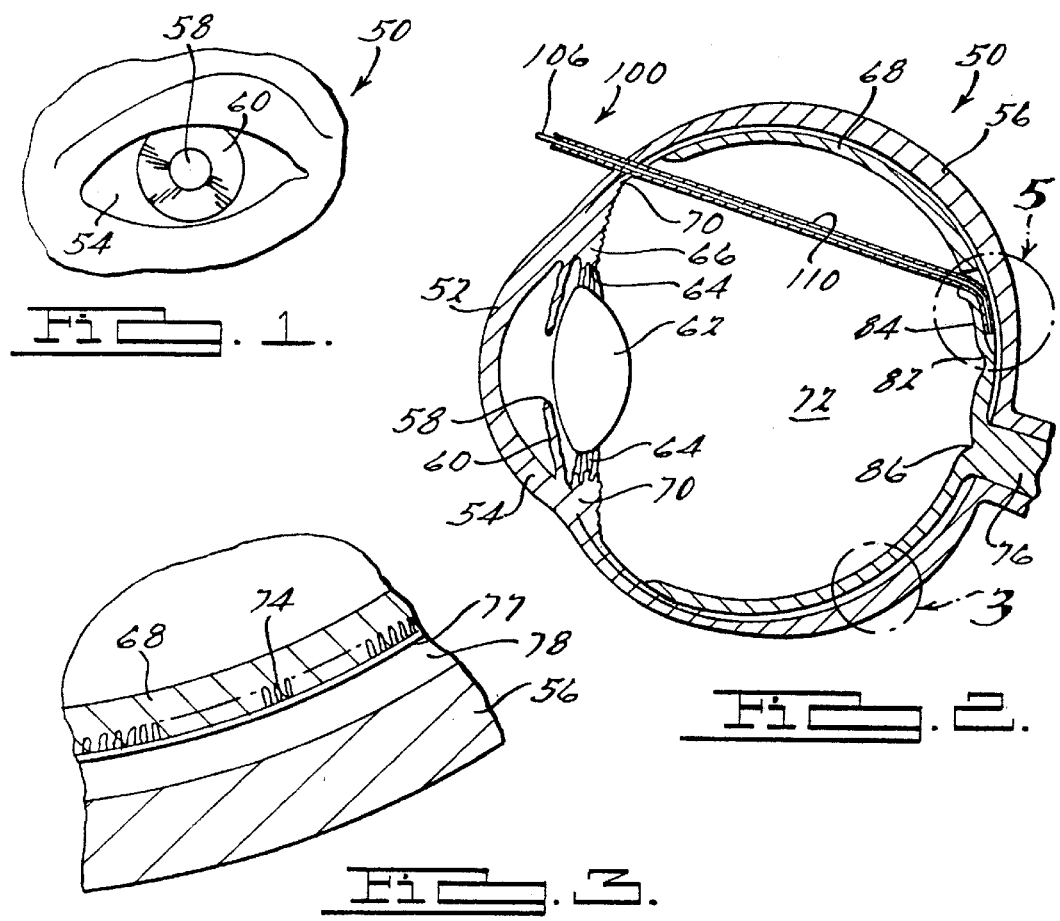
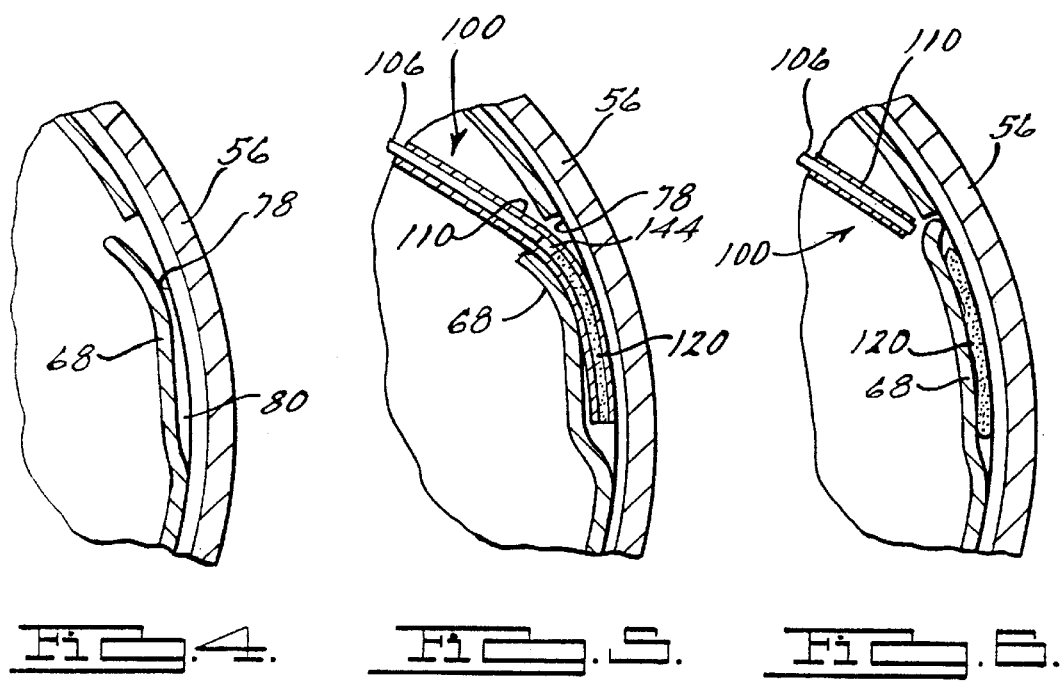

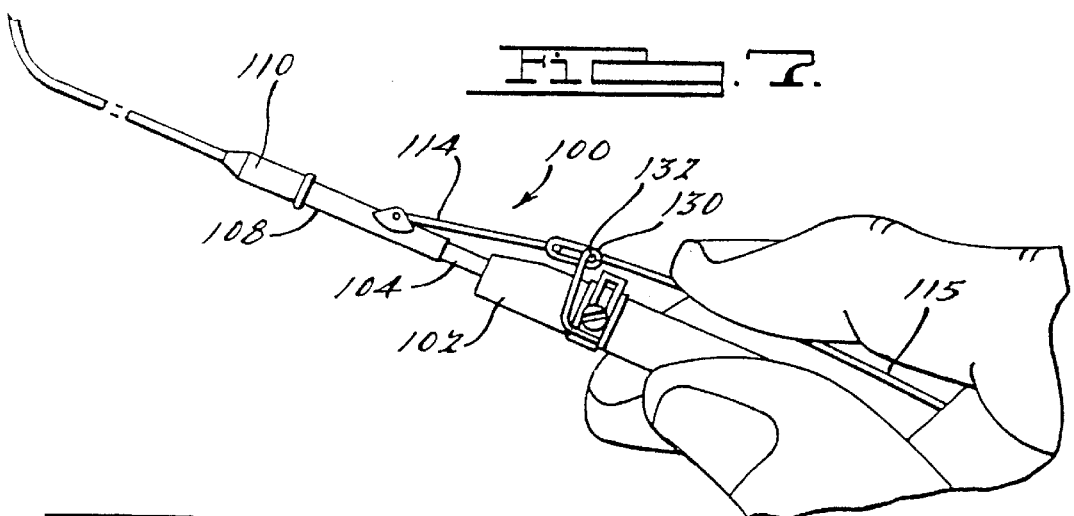
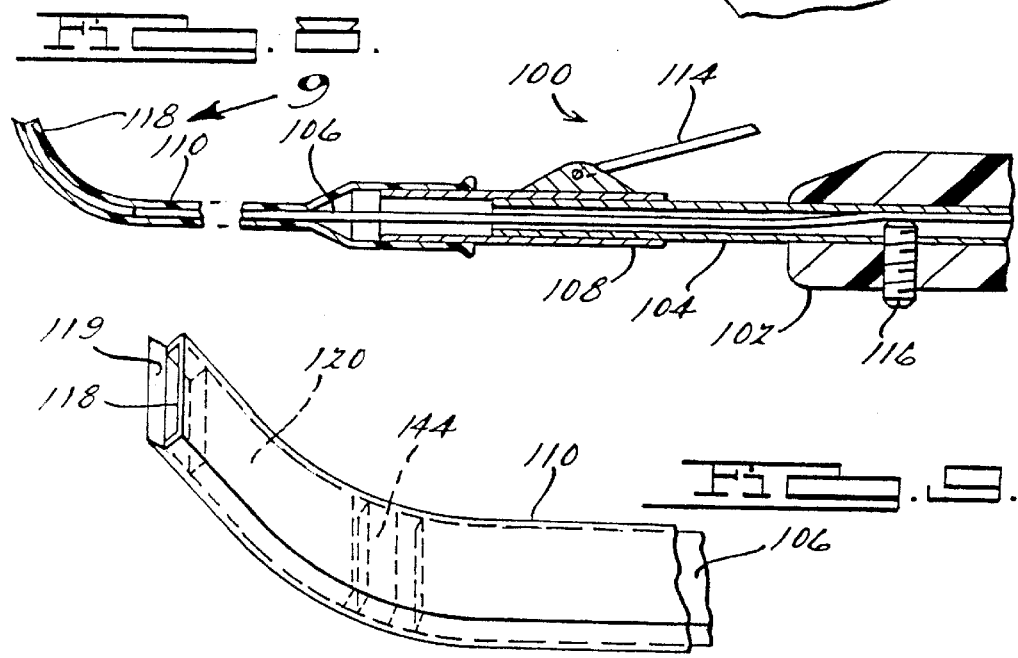
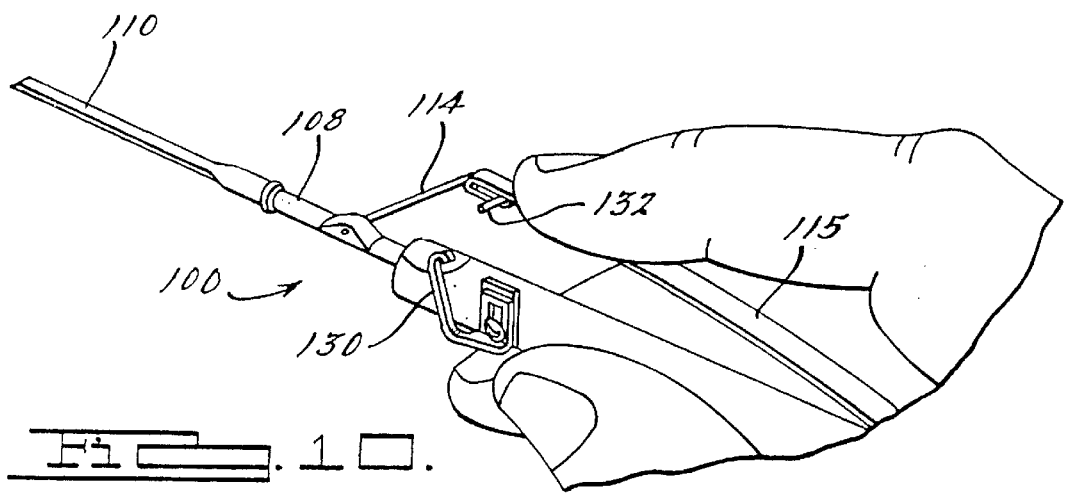

RETINAL TISSUE IMPLANTATION TOOL

BACKGROUND OF THE INVENTION

The present invention relates to an instrument and method for implanting delicate tissue and/or materials in the human body, more particularly to an instrument and method for surgically restoring eyesight by implanting fetal retinal tissue into the subretinal space in the back of the eye.

Most common eye problems, for example, myopia (nearsightedness), hyperopia (farsightedness), astigmatism (asymmetrical cornea, and presbyopia (the inability to focus on an object at close range) are due to errors in the refraction of light by the lens and cornea in the anterior part of the eye. Generally, these problems can be corrected by glasses, contact lenses, or corrective surgery.

However, blindness is most commonly due to damage of the retina in the back of the eye and, more specifically, is caused by abnormalities in the so-called "subretinal space" under the retina.

The transparent, layered retina processes light images projected by the cornea and lens. The photoreceptor layer in the back of the retina transforms the light into electrical impulses. Other retinal layers transfer these impulses through the optic nerve to the brain which interprets the impulses into what we perceive as sight.

The subretinal space is the area between the retinal pigment epithelium (RPE) and the photoreceptors of the retina.

Normally, the photoreceptors are in close contact with the RPE. The RPE has many functions. It provides nutrition for the photoreceptors, and also removes waste products from the photoreceptors. In a normal eye, there are no blood vessels in the subretinal space. However, in some retinal diseases, blood vessels and connective tissue can grow in this space and cause blindness. Under certain disease conditions, the photoreceptors can be detached very easily from the RPE. The photoreceptors will then degenerate, resulting in vision loss or blindness, while the other layers of the retina may remain functional. By replacing the diseased RPE and/or photoreceptors that can hook up to the functional part of the retina, vision may be restored.

The most frequent cause of legal blindness is macular degeneration and retinitis pigmentosa. The macula is located in the back of the eye in the central portion of the retina and is responsible for central vision. In patients with macular degeneration, there is initially a dysfunction of the RPE in the macular region, which later leads to ingrowth of blood vessels and destruction of the light-sensitive photoreceptors in the overlying retina. This results in impairment of central vision. Age related macular degeneration is an example of an eye disease that can be delayed by using the herein disclosed method and instrument.

Retinitis pigmentosa is a term for genetically caused photoreceptor degeneration. In these patients, the photoreceptors must be replaced. Again, the method and instrument of the present invention can be utilized.

It is to be noted that surgical correction of diseases in the subretinal space between the retina and the RPE is rendered extremely difficult by the environment in which the surgery must take place. Moreover, the surgical procedure disclosed herein to implant fetal retinal tissue into the subretinal space of the eye is complicated by the fact that fetal retinal tissue is in the nature of a transparent gelatinous mass and therefore extremely fragile.

SUMMARY OF THE INVENTION

In accordance with the present invention, we have developed an unique implantation instrument and procedure capable of handling fetal retinal tissue and placing this tissue into the subretinal space between the retinal pigment epithelium and the retina of the human eye.

We have discovered that intact sheets of fetal retinal tissue can be transplanted into the subretinal space by flattening and protecting it by a gel that disintegrates and is subsequently absorbed by the recipient eye so as to leave the transplant free. The transplant develops organized parallel layers resembling normal retina, with fully developed photoreceptors. The transplant can replace diseased photoreceptors and/or RPE. Moreover, the fetal retinal tissue is immunologically tolerated in the subretinal space and is not subject to rejection provided there is little surgical trauma.

The instrument of the instant invention comprises a handpiece for the support of a mandrel, a sleeve support telescoped over the mandrel, a tubular sleeve slidably journaled on the sleeve support, a nozzle mounted on the sleeve and extending over the mandrel, and a toggle mechanism that controls the position of the nozzle relative to the mandrel. The handpiece, mandrel, sleeve support, sleeve and toggle mechanism are preferably made of stainless steel to facilitate autoclaving. The nozzle is molded from elastic plastic. However, the instrument can be manufactured primarily from plastic if desired, so as to be disposable.

Advancement and retraction of the sleeve and nozzle relative to the handpiece and mandrel is controlled by the toggle mechanism on the handpiece, one element of which is a spring. When the spring element of the toggle mechanism is pressed toward the handpiece, the sleeve and the nozzle thereon move outwardly on the mandrel creating a space in the tip of the nozzle that, when placed in a fluid, exhibits a partial vacuum that draws tissue thereinto.

When the tissue is in place inside the nozzle tip, a toggle lock engages a peg on the spring element so as to lock the spring element and, therefore, the sleeve relative to the mandrel. The surgeon inserts the instrument on the target and holds his hand absolutely still. With a slight pressure on the spring element, without movement of the handpiece, the toggle lock is released, and the sleeve and nozzle retracts over the mandrel under the bias of the toggle spring, exposing and placing the tissue at the desired location.

The position of the toggle lock can be regulated so as to determine the space between the mandrel tip and the nozzle tip thereby adapting the instrument to the size of the transplant.

Broadly stated, the method of the invention comprises the steps of a) incising the eye through the pars plana in the region of the ciliary body at the periphery of the retina; b) incising the retina near the diseased target area giving access to the subretinal space; c) inserting the nozzle with the retinal tissue disposed in the tip thereof through the pars plana incision; d) inserting the nozzle tip through the retinal incision until the tip of the nozzle is placed into the subretinal target area; e) retracting the nozzle onto the mandrel of the instrument to expose and place the embedded, protected, and intact sheet of fetal retinal tissue under the retina; f) withdrawing the instrument from the target area; and g) flattening the retina by a special gas or gel.

Mandrels and nozzles can be customized in different sizes and shapes for implantation of different kinds of fragile tissue; gels containing different trophic factors or drugs; or electronic microchips into the subretinal space. Mandrels and nozzles can be produced in sterile packages for one-time use.

The procedure to protect the fragile fetal donor tissue after the dissection involves embedding and flattening the tissue without touching it. A special transfer pipette is used to transfer the tissue enveloped in a conventional transfer medium to a liquid gel that later solidifies. One type of recipient gel, for example collagen, solidifies at 37° C. Another type of gel, for example alginate, solidifies by adding a hardening component. Capillary action effects spreading of the drop of gel containing the tissue and flattening of the tissue therein. The gel is then solidified. The embedded tissue is stored on ice and covered with a tissue culture medium to prevent it from drying out. The embedded tissue is cut to fit the size of the chosen nozzle prior to introduction into the nozzle of the implantation instrument.

The details of the instrument and procedure of the invention are more fully described in the following specification and drawings.

BRIEF DESCRIPTION OF THE DRAWINGS

FIG. 1 is a frontal view of the human eye;

FIG. 2 is a cross-sectional view of the human eye showing the implantation instrument inserted through the pars plana into the subretinal space;

FIG. 3 is an enlarged view taken within the circle "3" of FIG. 2;

FIG. 4 is an enlarged view of the area within the circle "5" prior to insertion of the instrument nozzle into the subretinal space;

FIG. 5 is a view, similar to FIG. 4, with the instrument nozzle in the subretinal space;

FIG. 6 is a view, similar to FIG. 5, with the instrument nozzle retracted and the retinal tissue in the target area of the subretinal space;

FIG. 7 is a view of the instrument of the invention in the loaded condition;

FIG. 8 is a cross sectional view of the instrument of FIG. 7;

FIG. 9 is an enlarged perspective view taken within the circle "9" of FIG. 8;

FIG. 10 is a view of the instrument in the unloaded condition;

DETAILED DESCRIPTION OF THE PREFERRED EMBODIMENT(S)

Figure 11:
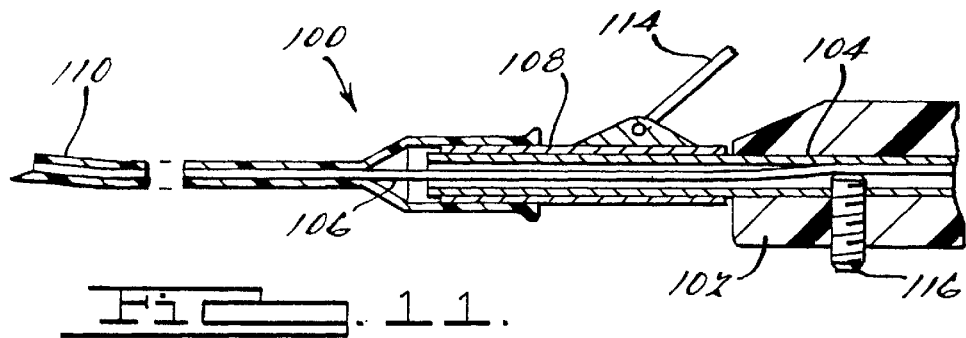
FIG. 11 is a cross sectional view of the instrument of FIG. 10.
Figure 13:
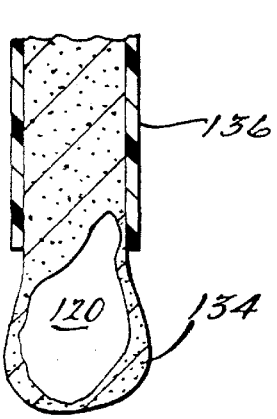
FIG. 13 is a view of a piece of retinal tissue about to be discharged from the transfer tool of FIG. 12.
Figure 14:
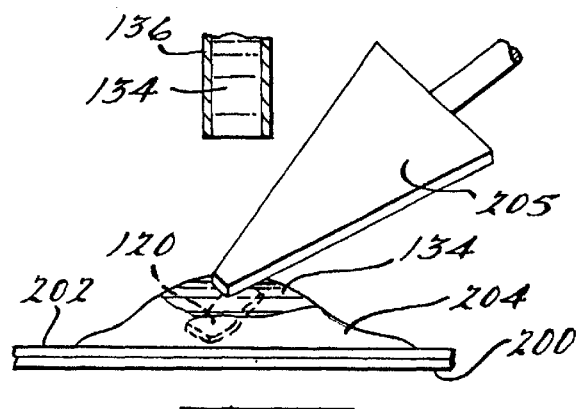
FIG. 14 is a view of a surgical sponge effecting removal of transfer fluid after disposition of retinal tissue in a protective gel.
Figure 15:
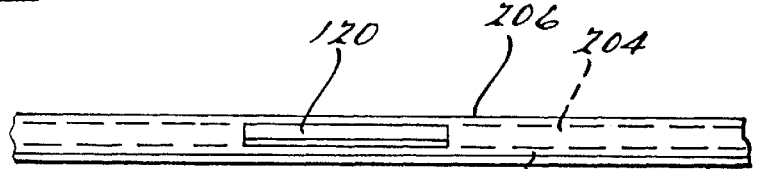
FIG. 15 is a view of the retinal tissue enveloped in gel for protection.
Figure 12:
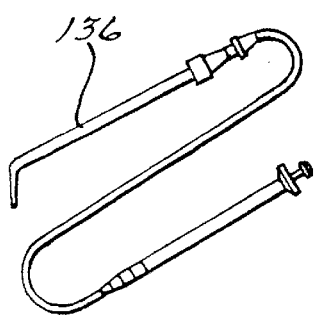
FIG. 12 in an elevational view of a tissue transfer pipette and syringe.

The environment in which the present invention has particular utility is illustrated in FIGS. 1 and 2 of the drawings. The front of the eye 50 is covered by a transparent tissue, the cornea 52, surrounded by white conjunctive tissue 54. The sclera 56 is hard fibrous tissue that covers the exterior of the eyeball. The pupil 58 is the opening through which light passes to the back of the eye. The iris 60 changes the size of the pupil 58 to adjust to the amount of light. The transparent lens 62 is located behind the iris 60 and is suspended by a net of fibers 64. The fibers 64 are attached to the ciliary body 66 that extends to where the retina 68 begins. The part of the ciliary body 66 adjacent to the retina 68 is called pars plana 70. The lens 62 focuses light rays onto the retina 68. The bulk of the eyeball 50 behind the lens 62 is formed by the vitreous chamber 72, which is filled with a colorless, gelatin like substance.

The retina 68 covers most of the wall of the vitreous chamber 72 and comprises transparent layers that extend forwardly to the pars plana 70 and which processes light images projected from the cornea 52 and the lens 62.

The rear of the retina 68 contains photoreceptors 74, which transform light into electrical impulses. The electrical impulses are carried by nerves in the retina 68 to the optic nerve 76, which, in turn leads to the brain. A monolayer of cells termed the retinal pigment epithelium (RPE) 77 resides behind the retina 68. The choroid 78 is a layer of blood vessels behind the RPE 77, that supplies oxygen and nutrients essential to the function of the eye 50. The RPE 77 transports these nutrients to the retina 68 and maintains a barrier between choroid 78 and retina 68.

The region between the retina 68 and the RPE 77 is called the subretinal space 80 (FIGS. 4–6). Normally, there is no "space". However, the retina 68 detaches very easily from the RPE 77 and it is in this "space" that the surgeon transplants the new piece of retinal tissue to replace damaged photoreceptors 74 and/or RPE 77.

The fovea 82 is a small depression in the center of the retina 68 that is essential for sharp (focussed) vision as well as color vision. The small area surrounding the fovea 82 is known as the macula 84 and is responsible for central vision. The point at which the optic nerve 76 leaves the retina 68 on its way to the brain is called optic disc 86.

In accordance with the present invention, surgical correction of retinal diseases in the subretinal "space" 80 between the retina 68 and the RPE 77 is facilitated by a novel implantation instrument 100.

As seen in FIGS. 7 through 11, the instrument 100 comprises a handpiece 102, a tubular sleeve support 104, a mandrel 106 disposed internally of the sleeve support 104, a sleeve 108 slidably journaled on the sleeve support 104, and a nozzle 110 mounted on the sleeve 108. A toggle mechanism comprising a rigid link 114 and a spring link 115 controls advancement and retraction of the sleeve 108 and nozzle 110 relative to the mandrel 106. The handpiece 102, sleeve support 104, mandrel 106, sleeve 108 and toggle links 114 and 115 can be made of stainless steel to facilitate autoclaving. The instrument can also be made disposable by using plastic with some metal parts.

The mandrel 106 comprises an elongated flat and narrow strip of steel that is fixed in the handpiece 102 by a screw 116 so as to be longitudinally adjustable relative thereto. Extension or retraction of the mandrel 106 relative to the housing 102 regulates its longitudinal position relative to the length of the plastic nozzle in the retracted position (FIG. 10).

The fit between the plastic nozzle 110 and the mandrel 106 must permit relative movement, but induce a suction in a tip portion 118 of the nozzle 110 when the nozzle 110 is advanced over the mandrel 106 thereby to induct a rectangular piece of retinal tissue 120. Alternatively, relatively hard implants can be inserted manually into the tip 118 of the nozzle 110.

The nozzle 110 is molded of elastic plastic, for example fluorinated ethylene propylene, so as to have a curvature at the tip 118 thereof in order to slide under the retina 68 into the subretinal "space" 80. Because of its elasticity, the curved nozzle tip 118, when retracted, will straighten out over the mandrel 106 so as to deposit implant tissue at the target area behind the retina 68. It is to be noted that the tip of the nozzle 118 has smooth edges and, to facilitate uptake of the retinal tissue 120, may be provided with a small lip 119 to aid in induction of the retinal tissue 120.

Advancement and retraction of the sleeve 108 and nozzle 110 is controlled by the rigid toggle link 114 and spring element 115 on the handpiece 102. When the spring element 115 of the toggle mechanism is pressed toward the handpiece 102, the sleeve 108 and the nozzle 110 are driven forwardly, relative to the mandrel 106, by the rigid toggle link 114 resulting in a partial vacuum internally of the tip portion 118 of the nozzle 110 that draws the retinal tissue 120 thereinto. When pressure on the spring element 115 of the toggle mechanism is released, the sleeve 108 and the nozzle 110 thereon is retracted over the mandrel 106, exposing and placing the retinal tissue 120 at the desired location.

The spring element 115 of the toggle mechanism can be locked in place by a toggle lock 130 that is engageable on a peg 132 on the spring element 115. A slight pressure on the spring element 115 releases the toggle lock 130 allowing the nozzle 110 to retract over the mandrel 106 under the bias of the spring element 115 thereby depositing the retinal tissue 120 in the target area vacated by the tip portion 118 of the nozzle 110.

In practicing the method of the invention, the surgeon first places an incision in the pars plana 70 of the eye 50. A small incision is then made in, for example, the macular region 84 of the retina 68. If necessary, abnormal tissue is removed from the subretinal "space" 80 between the retina 68 and the RPE 77. The nozzle 110 of the instrument 100, with the retinal tissue 120 enclosed in the curved nozzle tip 118 thereof, is inserted through the incision in the pars plana 70 and through the incision in the retina 68 until the tip of the nozzle 118 is orientated over the target area in the subretinal "space" 80.

Slight pressure on the spring element 115 of the instrument 100 then releases the toggle lock 130 from the pin 132 allowing the spring element 115 and rigid link 114 of the toggle mechanism to effect retraction of the nozzle 110 and deposition of the retinal tissue 120. It is to be noted that the handpiece 102 and mandrel 106 of the instrument 100 are not required to move incident to deposition of the retinal tissue 120 allowing the surgeon to precisely position the tissue.

From the forgoing, it should be apparent that the instrument of the present invention is ideally suited for precisely placing implants into the eye. The surgeon has only to keep his hand still and exert a slight pressure on the spring element 115 of the instrument 100 to release the toggle lock 130 conditioning the instrument 100 itself to effect retraction of the nozzle 110 and placement of the implant on the target.

Figure 16:
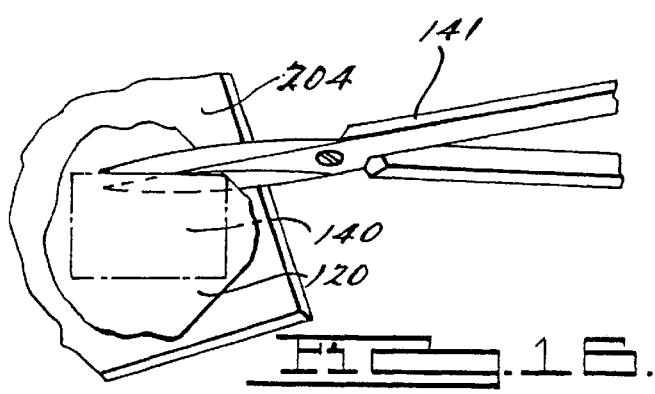
FIG. 16 is a view of the retinal tissue being sized for induction into the nozzle of the instrument of the invention.

In practice of the disclosed application of the present invention, fetal human retinal tissue is harvested according to established procedures. Small pieces of retinal tissue are stored in a conventional hibernation medium on ice. As seen in FIG. 16 a piece of retinal tissue 120 is transported in a conventional transport medium 134 in a transfer pipette 136. Preparations are made for the reception of the retinal tissue 120 by coating a dish 200 with a thin layer of embedding gel 202 which is then cooled or polymerized, depending on the type of gel, by incubation at 37° C. or addition of a hardener, respectively. A 50–100 µL drop of embedding gel is placed onto the coated dish 200, which forms a layer 204 for the reception of the retinal tissue 120. After the retinal tissue 120 is deposited, the transfer medium 134 surrounding the retinal tissue 120 is removed by a surgical sponge 205 to prevent dilution of the layer 204 of embedding gel. The retinal tissue 120 is flattened as by capillary spreading of the drop of embedding gel forming the layer 204. An additional small drop, for example 10–20 µL, of embedding gel is deposited over the layer 24 to form an overlying layer 206. The layers of embedding medium 202, 204 and 206 with the retinal tissue 120 embedded therein are then cooled or polymerized so as to be transformed into a gel that protects the embedded retinal tissue 120.

After the embedding medium is properly cooled or polymerized, a conventional hibernation medium is added to the dish 200 to prevent drying of the retinal tissue 120. The retinal tissue 120 is thereafter stored on ice until use.

When ready for surgery, the retinal tissue 120 is cut, as by a microscissors 141, into a rectangular section 140 for acceptance into the nozzle 110 of the implantation instrument 100. Initially, a small piece of gel 144 is placed adjacent the mandrel 106 in the nozzle 110 of the implantation instrument 100 to prevent the retinal tissue 120 from adhering to the mandrel 106. The sized piece of retinal tissue 120 is then inducted into the tip 118 of the nozzle 110. When the piece of retinal tissue 120 is properly enclosed within the nozzle 110 of the instrument 100, the lock pin 132 on the spring element 115 of the toggle mechanism is engaged in the toggle lock 130.

After preparation of the eye for surgery, the tip 118 of the nozzle 110 on the instrument 100 is inserted into the target area of the eye behind the retinal flap. When the tip 118 of the nozzle 110 is orientated directly over the target, the surgeon applies a slight pressure on the spring element 115 of the toggle mechanism thereby releasing the lock pin 132 from the toggle lock 130. The nozzle 110 is retracted relative to the mandrel 106 due to the bias of the spring element 115, depositing the retinal tissue 120 directly on the target. After deposit of the retinal tissue 120, the surgeon retracts the instrument 100 from the eye 50.

It is to be noted that, in accordance with an important feature of the present invention, the surgeon's hand, handpiece 102 and mandrel 106 are stationary while the nozzle 110 of the instrument 100 retracts to effect placement of the implant.

We claim:

1. A method of placing an implant in a target area within the human body comprising the steps of:

orientating said implant in an open end of an elongated tubular nozzle having a mandrel slidably telescoped internally thereof;

incising the body for the acceptance of said nozzle;

inserting said nozzle through the incision in the body so as to orientate the open end of said nozzle over the target area in the body; and retracting the open end of said nozzle over said mandrel to deposit said implant over the target area in the body.

2. An instrument for inserting an implant in a target area within the human body comprising:

an elongated mandrel;

a tubular nozzle telescoped over said mandrel and slidable longitudinally thereof; and a nozzle control linkage connected to said nozzle and to said mandrel, movement of said control linkage relative to said mandrel effecting movement of said nozzle relative to said mandrel.

3. The instrument of claim 2 wherein said mandrel is supported by a handpiece and said control linkage comprises a toggle mechanism having a one end connected to said nozzle and an opposite end connected to said handpiece.

4. The instrument of claim 3 including latching means on said handpiece engageable with said toggle mechanism to preclude relative movement therebetween.

5. The instrument of claim 4 wherein the latching means on said handpiece is releasable to permit movement of said toggle mechanism so as to effect relative movement of said nozzle relative to said mandrel.

6. An instrument for inserting an implant into a human eye comprising:
- an elongated mandrel;
- a tubular nozzle telescoped over said mandrel and slidable longitudinally thereof; and
- a nozzle control linkage connected to said nozzle and to said mandrel, movement of said control linkage relative to said mandrel effecting movement of said nozzle relative to said mandrel.

* * * * *

UNITED STATES PATENT AND TRADEMARK OFFICE
CERTIFICATE OF CORRECTION

PATENT NO. : 6,159,218
DATED : December 12, 2000
INVENTOR(S) : Aramant et al.

It is certified that error appears in the above-identified patent and that said Letters Patent is hereby corrected as shown below:

Column 1,
Line 2, the following should be added:
-- Research for this invention was made with support from the National Institute of Health Grant Number R01EY08519. The Government has rights to this invention. --.

Signed and Sealed this

Thirteenth Day of December, 2005

JON W. DUDAS
*Director of the United States Patent and Trademark Office*